United States Patent
Freeland et al.

(10) Patent No.: US 9,546,937 B2
(45) Date of Patent: Jan. 17, 2017

(54) TISSUE CASSETTE ASSEMBLY

(71) Applicants: Richard-Allan Scientific Company, Kalamazoo, MI (US); Western Michigan University Research Foundation (WMURF), Kalamazoo, MI (US)

(72) Inventors: Jennifer H. Freeland, Portage, MI (US); Keith O. Whittlinger, Penfield, NY (US); Parviz Merati, Kalamazoo, MI (US); Nathanael J. Cooper, Avon, IN (US)

(73) Assignees: Richard-Allan Scientific Company, Kalamazoo, MI (US); Western Michigan University Research Foundation (WMURF), Kalamazoo, MI (US)

( * ) Notice: Subject to any disclaimer, the term of this patent is extended or adjusted under 35 U.S.C. 154(b) by 31 days.

(21) Appl. No.: 13/749,256

(22) Filed: Jan. 24, 2013

(65) Prior Publication Data
US 2013/0196371 A1 Aug. 1, 2013

Related U.S. Application Data

(60) Provisional application No. 61/591,132, filed on Jan. 26, 2012.

(51) Int. Cl.
*A61B 10/00* (2006.01)
*G01N 1/36* (2006.01)

(52) U.S. Cl.
CPC ..................... *G01N 1/36* (2013.01)

(58) Field of Classification Search
CPC ...................................................... G01N 1/36
USPC ...................................... 422/63–67, 500–503
See application file for complete search history.

(56) References Cited

U.S. PATENT DOCUMENTS

| | | | | |
|---|---|---|---|---|
| 4,220,252 A | * | 9/1980 | Beall | B65D 43/162 220/266 |
| 4,421,246 A | * | 12/1983 | Schultz | G01N 1/36 206/205 |
| 4,549,670 A | | 10/1985 | Trendler | |
| 4,801,553 A | | 1/1989 | Owen et al. | |
| 5,061,452 A | * | 10/1991 | Yamamoto et al. | 422/536 |
| 5,080,869 A | * | 1/1992 | McCormick | G01N 1/312 422/500 |
| 5,127,537 A | | 7/1992 | Graham | |
| 5,269,671 A | | 12/1993 | McCormick | |

(Continued)

*Primary Examiner* — Jyoti Nagpaul
(74) *Attorney, Agent, or Firm* — Workman Nydegger (57) ABSTRACT

A tissue cassette includes a body having a first floor and a first perimeter wall encircling and extending from the first floor so that the first floor and first perimeter wall at least partially bound a body cavity, the first floor having a plurality of spaced apart openings extending therethrough. A mold has a second floor and a second perimeter wall encircling and extending from the second floor so that the second floor and second perimeter wall at least partially bound a mold cavity, the second floor having at least one micropore extending therethrough, the at least one micropore having a maximum diameter less than 0.040 inches. A hinge couples the body to the mold so that the body and mold can move between a closed position wherein the first floor overlies the second floor so as to form a tissue compartment therebetween and an open position.

11 Claims, 12 Drawing Sheets

(56) References Cited

U.S. PATENT DOCUMENTS

| | | | |
|---|---|---|---|
| 5,817,032 A * | 10/1998 | Williamson et al. | 600/562 |
| 6,017,476 A * | 1/2000 | Renshaw | G01N 1/36 |
| | | | 264/158 |
| D448,487 S | 9/2001 | Saez et al. | |
| 7,156,814 B1 * | 1/2007 | Williamson et al. | 600/562 |
| 7,547,542 B2 | 6/2009 | Bjornsen | |
| 2007/0116612 A1 | 5/2007 | Williamson, IV | |
| 2008/0044895 A1 | 2/2008 | Wedell et al. | |
| 2008/0138854 A1 | 6/2008 | Williamson | |
| 2010/0278627 A1 | 11/2010 | Williamson, IV et al. | |

* cited by examiner

TISSUE CASSETTE ASSEMBLY

CROSS-REFERENCE TO RELATED APPLICATIONS

This application claims the benefit of Provisional Application No. 61/591,132, filed Jan. 26, 2012, which is incorporated herein by specific reference.

BACKGROUND OF THE INVENTION

1. The Field of the Invention

The present invention relates to tissue cassette assemblies and methods of use.

2. The Relevant Technology

To accurately diagnose a diseased tissue sample, the tissue sample is first processed to remove the water content. Next, the tissue sample is embedded in paraffin wax, following which a microtome is used to cut thin slices of the tissue. A pathologist is then able to analyze the thin slices to diagnose the disease.

Tissue cassettes are commonly used in the processing step to assist in the removal of the water content from the tissue sample. Tissue cassettes come in a variety of different configurations and can be used in different methods. In one embodiment, the tissue cassette includes a base having a compartment for receiving a tissue sample and a lid that selectively covers the compartment to capture the specimen therein. A pair of sponges may be used within the cassette to sandwich in and prevent small specimen loss during tissue processing steps and/or to sandwich the tissue sample in a desired orientation. The pair of sponges may be omitted if the appropriate specimen size warrants.

With the tissue sample loaded in the tissue cassette, the compartment of the tissue cassette is sequentially flooded with a series of different solvents to remove the water content from the tissue sample. The tissue cassette has relatively large openings in both the lid and base that permit the solvents to freely flow into and out of the compartment for treating the tissue sample. Once the water content has been removed from the tissue sample, the tissue cassette is opened and the sponge(s) are removed and discarded. The tissue sample is placed into a separate mold and the cassette base is coupled to the mold. Liquid paraffin wax is then poured onto the tissue cassette so that the paraffin wax passes through the openings in the lid and the base so as to surround and enclose the tissue sample. The mold holding the tissue cassette acts as a cup to receive and hold the paraffin wax as it solidifies around the tissue sample. Once the paraffin wax has solidified, the frame is then used to mount the embedded tissue sample onto the microtome following which the desired slices can be obtained.

Although the above tissue cassette is functional for processing tissue samples, it has a number of shortcomings. For example, the sponges used for holding the tissue sample are not intended to become part of the final paraffin block-tissue-sample-cassette base assembly; they are intended to be discarded after processing and before embedding with molten paraffin. As such, the specifications of the sponge are not tightly held and vary widely. That is, the pore size, the density, the air-flow volume, and other parameters are not required to be held into a tight range of parameters. The sponge is non-reticulated, that is, a closed cell sponge, and is designed to sufficiently aid in the flow of tissue processing reagents during the tissue processing step, but is not intended to hold a tissue specimen in its final orientation within a paraffin block. It is assumed that a trained technologist re-orients all tissues into the final orientation at the embedding step. Because the parameters of this sponge are not required to be tightly held, fragments of the sponge can and do fragment and become lodged into the tissue sample, creating artificial sponge artifact on the slide. In addition, the sponge, with little resistance to pressure forced onto it by a tissue sample, can imprint its shape onto the tissue surface, introducing another form of artifact. Both forms of sponge artifact can and do create difficulty in proper sample analysis. During the processing stage, the tissue sample is sequentially exposed to a series of different reagents. As a result of the sponge retaining a reagent, the retained first reagent can contaminate the second reagent and make it less effective. More frequent reagent changes/reagent refreshing are required when using a pair of sponges.

Finally, as discussed above, the prior art requires that the tissue cassette be used with a separate frame and mold to enable embedding with paraffin wax and securing to the microtome. The required use of these additional parts increases the expense and slows the processing time. Accordingly, what are needed are systems and methods that address some or all of the above shortcomings and other deficiencies known in the art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

Figure 1:
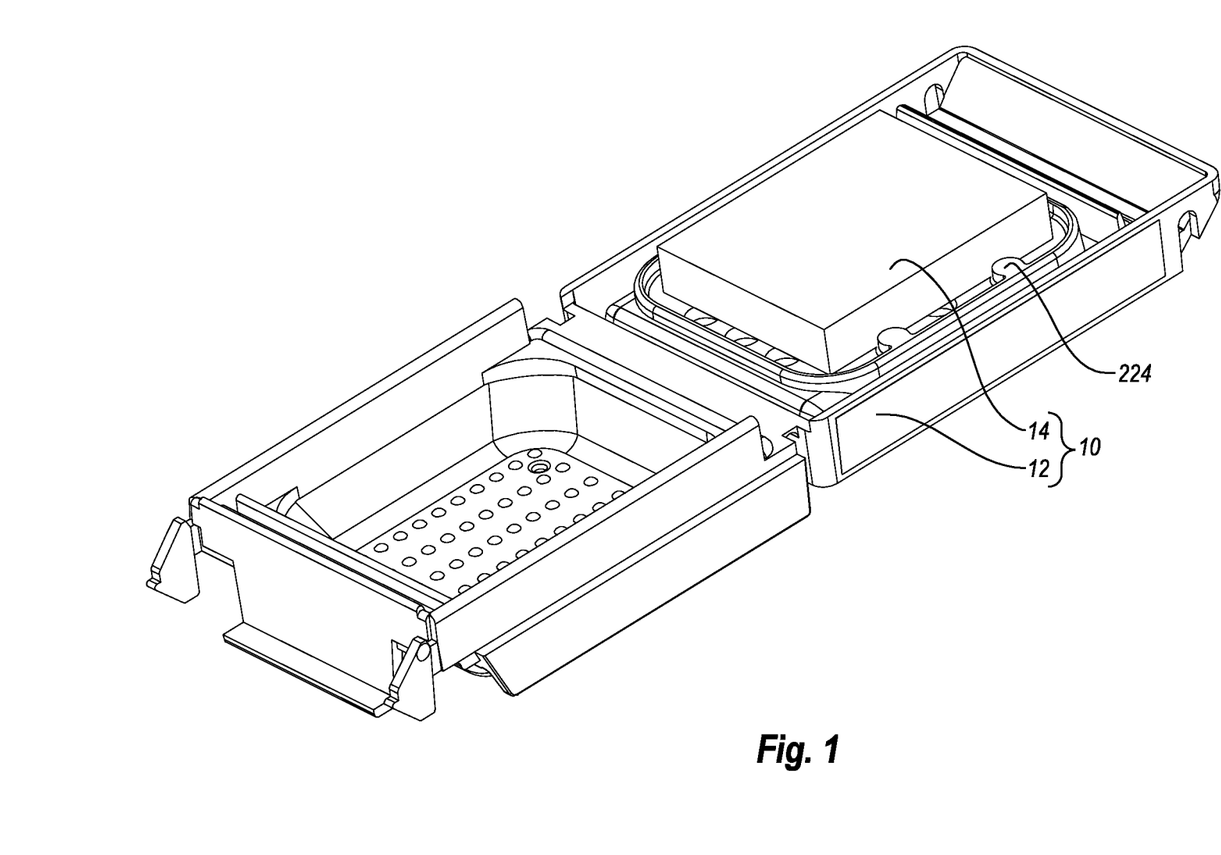
FIG. 1 is a perspective view of a tissue cassette assembly in an open position.

Depicted in FIG. 1 is one embodiment of an inventive tissue cassette assembly 10 incorporating features of the present invention. Tissue cassette assembly 10 is configured to hold a tissue specimen while the specimen is prepared for microtome sectioning. A portion of assembly 10 holding the prepared specimen can also be mounted directly to the microtome to assist in the sectioning process.

Figure 2:
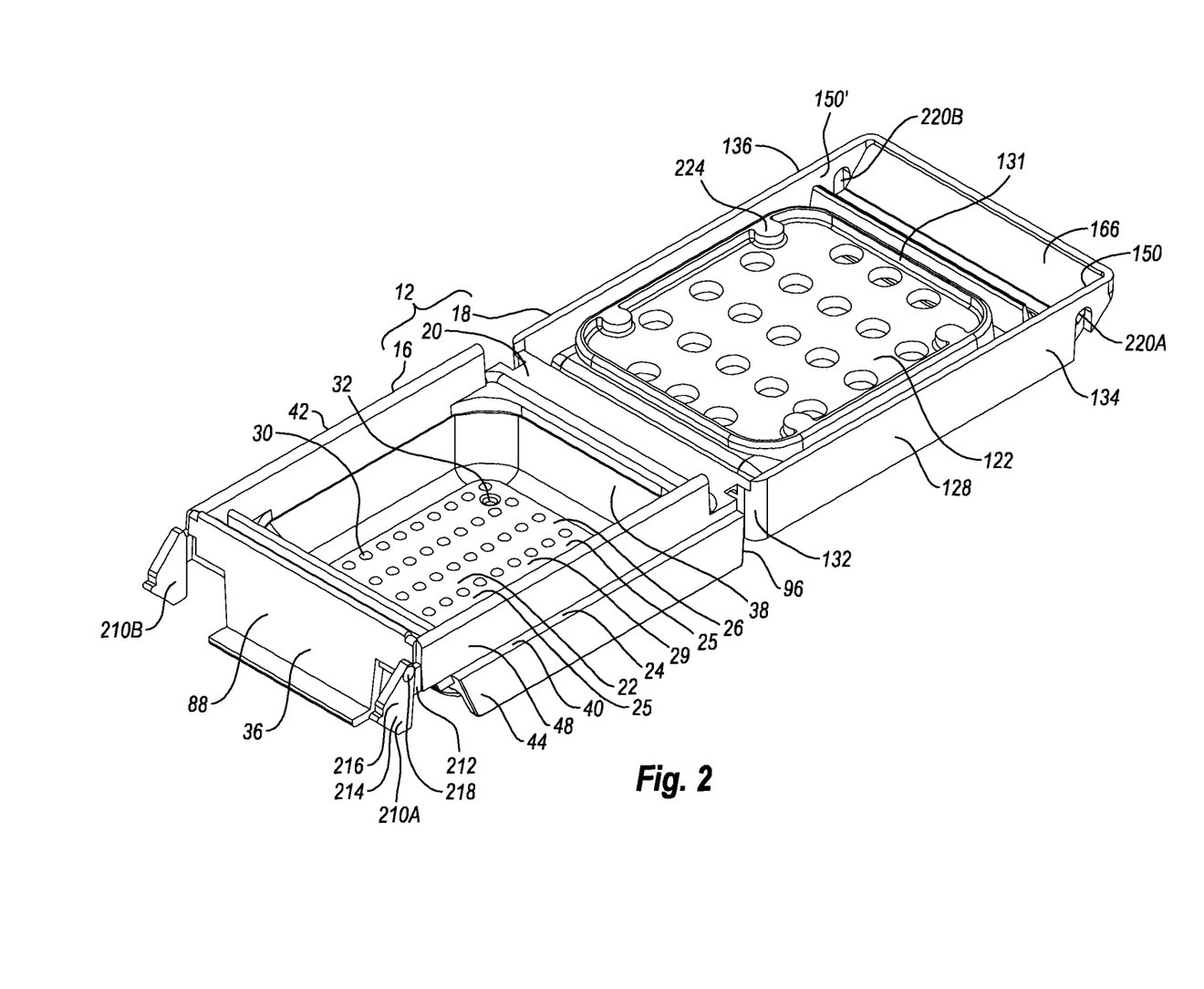
FIG. 2 is a top perspective view of the tissue cassette of the tissue cassette assembly shown in FIG. 1, the tissue cassette being in an open position.
Figure 4:
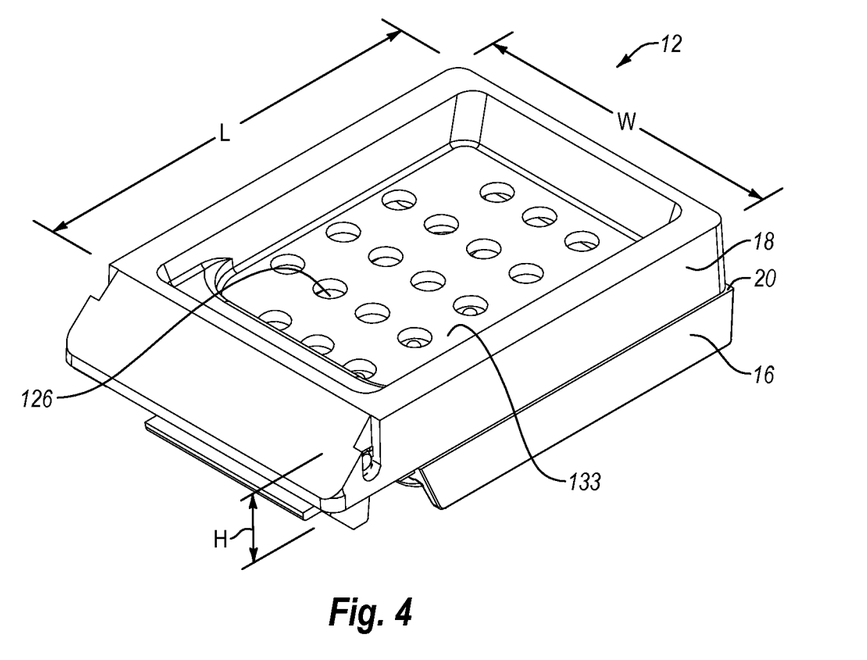
FIG. 4 is a top perspective view of the tissue cassette shown in FIG. 2 in a closed position.
Figure 8:
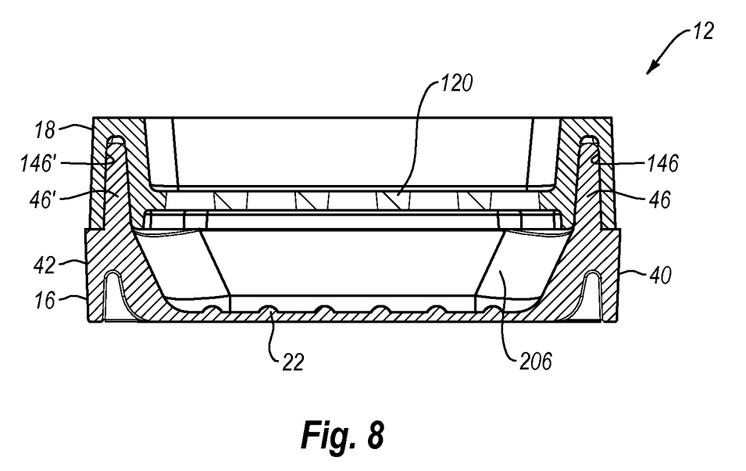
FIG. 8 is a lateral cross sectional side view of the tissue cassette shown in FIG. 4.

Tissue cassette assembly 10 comprises a tissue cassette 12 and an orientation device sponge 14 mounted thereto. Turning to FIG. 2, tissue cassette 12 comprises a mold 16, a base 18, and a hinge 20 extending therebetween. Hinge 20 enables tissue cassette 12 to be selectively folded between an open position and a closed position. In the open position, as shown in FIGS. 1 and 2, mold 16 and base 18 can be adjacently disposed in substantially horizontal alignment or are otherwise disposed so that mold 16 and base 18 are not overlapping. In the closed position, as shown in FIG. 4 and discussed below in greater detail, mold 16 and/or base 18 pivot about hinge 20 so that mold 16 and base 18 couple together and bound a tissue compartment 206 therebetween as shown in FIG. 8. As is also discussed below in greater detail, mold 16 and base 18 are specifically designed so that when tissue cassette 12 is in the closed position, an annular seal is formed at the engagement between mold 16 and base 18 so that when molten wax is poured within tissue compartment 206 the molten wax cannot leak out between mold 16 and base 18.

Figure 3:
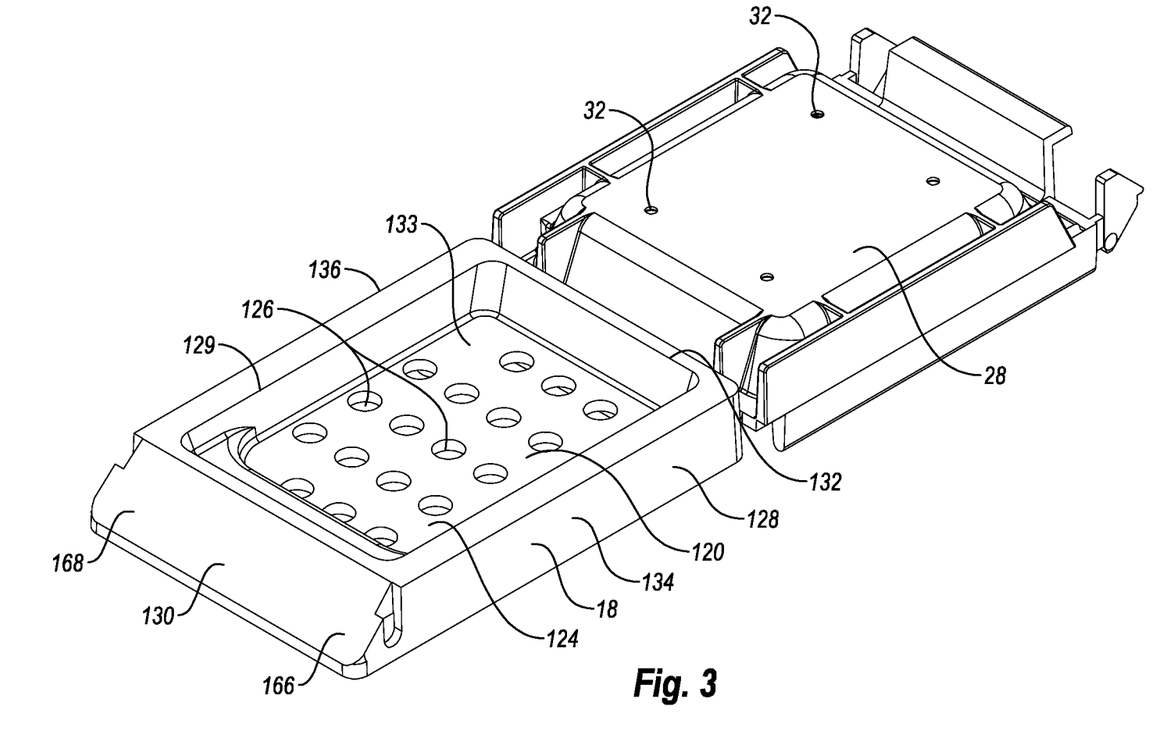
FIG. 3 is a bottom perspective view of the tissue cassette shown in FIG. 2.

Returning to FIG. 2, mold 16 comprises a floor 22 and a perimeter wall 24 that encircles and up-stands from floor 22. Floor 22 and perimeter wall 24 bound a mold cavity 25. More specifically, floor 22 has an inside face 26 and an opposing outside face 28 (FIG. 3). Inside face 26 is the surface on which the tissue sample rests during processing. Inside face 26 includes a sub-surface 29 that is substantially planar and a plurality of spaced apart projections 30 upstanding from sub-surface 29. In the embodiment depicted, projections 30 are in a form of rounded or semi-spherical bumps having a maximum diameter in a range between about 0.020 to about 0.030 inches and a maximum height in a range between about 0.010 to about 0.015 inches. Other dimension can be also be used. In alternative embodiments, it is appreciated that projections 30 can have a variety of alternative configurations such as oval, polygonal, irregular or the like and can be dispersed in a variety of different patterns. Projections 30 are used to partially support the tissue sample off of sub-surface 29 so that different processing fluids and waxes can completely encircle the tissue sample.

Extending through floor 22 between inside face 26 and outside face 28 are a plurality of micropores 32. As will be discussed below in greater detail, the number and size of micropores is selected so that the processing fluids, such as alcohols and xylenes, can freely flow into and out of the closed tissue cassette 12 through micropores 32 for properly processing the tissue sample therein while simultaneously minimizing the amount of molten wax that can flow out of micropores 32 during embedding of the tissue sample. The depicted micropores 32 are circular and have a maximum diameter in a range between about 0.030 to about 0.040 inches with about 0.033 to about 0.038 inches being more common. Micropores 32 commonly have a diameter less than 0.038 inches and more commonly less than 0.037 inches. Other dimensions can also be used.

The number of micropores 32 is typically in a range between 2 and 8 with 2 to 6 being common and 4 being most common. Micropores 32 can be disposed at a variety of different locations on floor 22 but are typically disposed adjacent to perimeter wall 24 to help preclude being blocked by the tissue sample resting on floor 22 or sponge 14. In alternative embodiments, micropores 32 can have a variety of alternative cross sectional configurations such as oval, polygonal, linear or irregular. In such alternative designs, each micropore typically has a cross sectional area in a range between about 0.015 to about 0.030 $in^2$ with about 0.020 to about 0.025 $in^2$ being more common. Other areas can also be used. The total number of openings extending through floor 22 including micropores 32 typically does not exceed 8 and more commonly does not exceed 6. The total cross sectional area of all openings extending through floor 22 typically does not exceed 0.020 $in^2$ and more commonly does not exceed 0.018 $in^2$.

Figure 5:
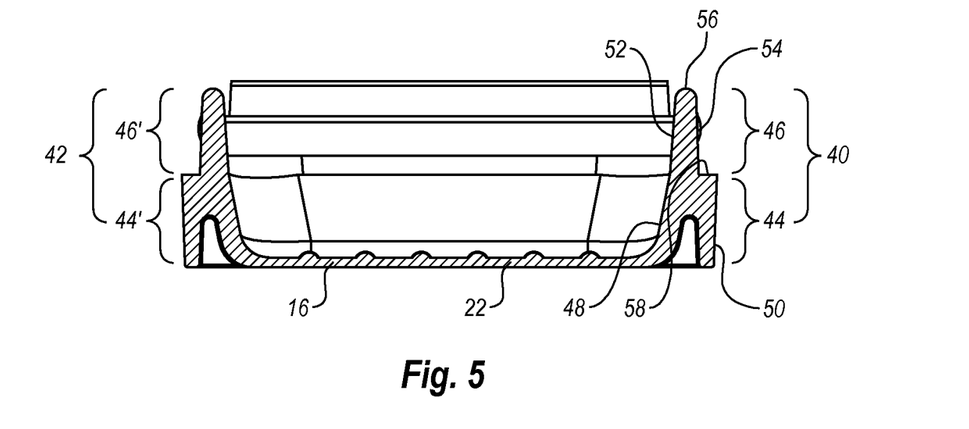
FIG. 5 is a lateral cross section side view of the mold of the tissue cassette shown in FIG. 2.

Perimeter wall 24 comprises a front wall 36 and an opposing back wall 38 with a pair of opposing side walls 40 and 42 extending therebetween. Side wall 40 comprises a boundary wall 44 and a sealing ridge 48 upstanding therefrom that both extend between front wall 36 and back wall 38. As depicted in FIG. 5, boundary wall 44 has an inside face 48 that slops up and away from floor 22 and a substantially vertical outside face 50. Sealing ridge 46 also has an inside face 52 and an opposing outside face 54 that both extend from the top of boundary wall 44 to a rounded end face 56. Sealing ridge 46 inwardly tapers in a generally V-shape configuration as it extends from boundary wall 44 to end face 56. Both inside face 52 and outside face 54 of sealing ridge 46 inwardly slope at an angle relative to vertical in a range between about 1° to about 10° with about 1° to about 5° being more common. A ledge 58 is formed on top of boundary wall 44 adjacent to outside face 54. The operation of sealing ridge 46 will be discussed below in greater detail.

Side wall 42 is the mirror image of side wall 40 and thus like elements are identified by like reference characters but with the addition of a prime (').

Figure 6:
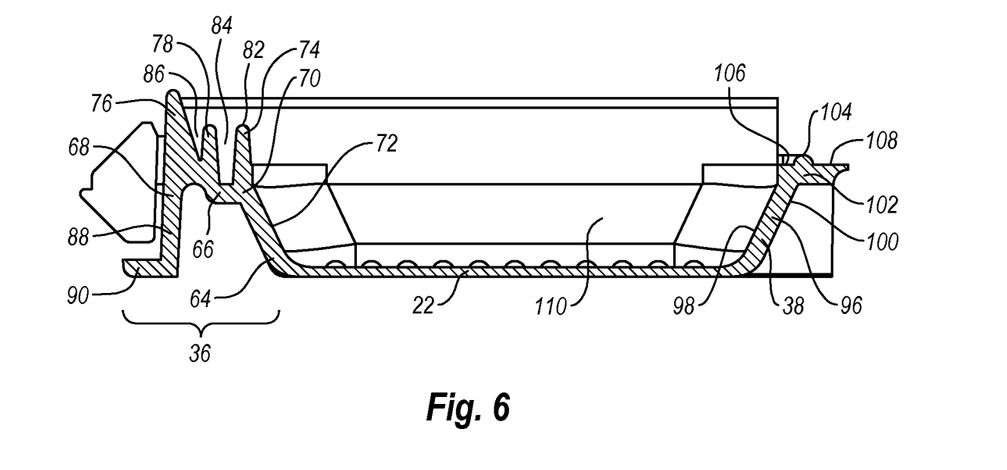
FIG. 6 is a longitudinal cross sectional side view of the mold shown in FIG. 5.

Turning to FIG. 6, front wall 36 comprises a platform 66 that extends between a first end 68 and an opposing second end 70. A boundary wall 64 extends from second end 70 of platform 66 to floor 22. Boundary wall 64 has an inside face 72 that slopes up and away from floor 22. Upwardly projecting from platform 66 is an inside sealing ridge 74 disposed at second end 70, an outside sealing ridge 76 disposed at first end 68, and a central sealing ridge 78 disposed between sealing ridges 74 and 76. Each of sealing ridges 74, 76 and 78 have a substantially V-shaped configuration with opposing side faces that slope inwardly as they extend to a corresponding end face 82. In the embodiment depicted, sealing ridges 74 and 78 have substantially the same height and both of the opposing faces typically slope at the angle as discussed above with regard to sealing ridge 46. A first sealing slot 84 is formed between sealing ridges 74 and 78 while a second sealing slot 86 is formed between sealing ridges 76 and 78. Each of platform 66, boundary wall 64, and sealing ridges 74, 76, and 78 longitudinally extend between opposing sidewalls 40 and 42.

A leg 88 projects down from first end 68 of platform 66 while a foot 90 projects forward from a lower end of leg 88. As depicted in FIG. 2, the upper end of leg 88 extends between opposing sidewalls 40 and 42 while the lower end of support leg 88 is notched on opposing ends so as to be shorter. Foot 90 has a bottom surface that is disposed in substantially the same plane as the bottom surface of floor 22. Leg 88 and foot 90 provide stability for the front end of mold 16. Furthermore, leg 88 and foot 90 providing a gripping surface for holing mold 16 when moving tissue cassette 12 from the closed to open position.

As also shown in FIG. 6, back wall 38 comprises a boundary wall 96 having a configuration complementary to boundary walls 44 and extending between opposing sidewalls 40 and 42. Boundary wall 96 has an inside face 98 and an opposing outside face 100. A ledge 102 is formed at an upper end of boundary wall 96. An elongated sealing ridge 104 upwardly projects from ledge 102 and extends along the length thereof. Ledge 102 comprises shoulders 106 and 108 that horizontally extend on opposing sides of sealing ridge 104. Boundary walls 44, 44', 64, and 96 combined with floor 22 to bind a mold cavity 110.

Returning to FIG. 3, base 18 comprises a floor 120 having an inside face 122 (FIG. 2) and an opposing outside face 124. A plurality of spaced apart openings 126 extend through floor 120. In the depicted embodiment, openings 126 are circular and have a diameter in a range between about 0.100 to about 0.110 inches with about 0.102 to about 0.106 inches being more common. In alternative embodiments, openings 126 can have a variety of different configurations such as elliptical, polygonal, linear, irregular or the like. Openings 126 can be uniformly distributed over floor 120 and have a cross sectional area in a range between about 3.125 to about 3.135 in$^2$. Other areas can also be used. A perimeter wall 128 encircles an outside edge of floor 120. A portion 129 of perimeter wall 128 projects up from floor 120 while another portion 131 (FIG. 2) of perimeter wall 128 projects down from floor 120. Floor 120 and portion 129 of perimeter wall 128 projecting up from floor 120 bound a base cavity 133.

Figure 7:
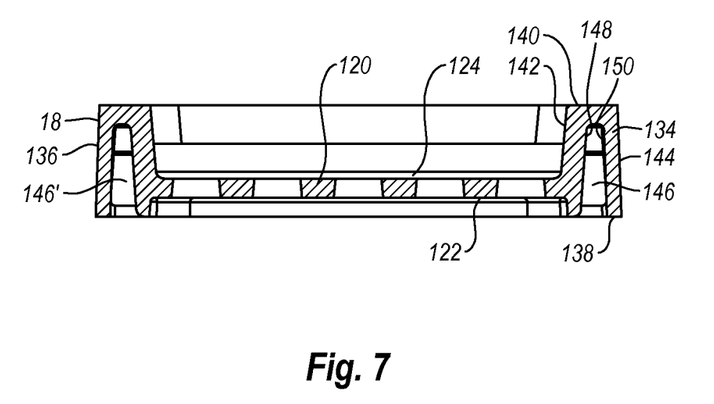
FIG. 7 is a lateral cross sectional side view of the base of the tissue cassette shown in FIG. 2.

Perimeter wall 128 comprises a front wall 130, an opposing back wall 132, and opposing side walls 134 and 136 extending therebetween. Turning to FIG. 7, side wall 134 comprises a bottom end face 138 and an opposing top end face 140 with an opposing inside face 142 and outside face 144 extending therebetween. A sealing slot 146 is recessed on bottom end face 138 and extends along the length side wall 134. Sealing slot 146 is bounded between opposing faces 148 and 150 and inwardly tapers as it extends from bottom end wall 138 to top end wall 140. More specifically, sealing slot 146 has a tapered configuration substantially complimentary to sealing ridge 46 (FIG. 5) and is located so that when tissue cassette 12 is moved to the closed position, as shown in FIG. 8, sealing ridge 46 is received within sealing slot 146. However, sealing slot 146 is dimensioned slightly smaller than sealing ridge 46 by an amount in a range between about 0.002 to about 0.006 inches so that sealing ridge 46 creates an interference fit as it is received within sealing slot 146. The configuration of sealing ridge 46 and sealing slot 146 along with the interference fit produced therebetween results in a seal formed between sealing ridge 46 and sealing slot 146 that prevents the passage of molten wax therebetween when, as will be discussed below in greater detail, molten wax is poured within closed tissue cassette 12.

Returning to FIG. 7, sidewall 136 of base 18 is the mirror image of side wall 134 and thus like elements are identified by like reference characters but with the addition of a prime ('). In view of the foregoing, sealing ridge 46' of sidewall 42 is received in an interference fit within sealing slot 146' when tissue cassette 12 is moved to the closed position. Again, this engagement prevents molten wax from passing therebetween when molten wax is poured within closed tissue cassette 12.

Figure 9:
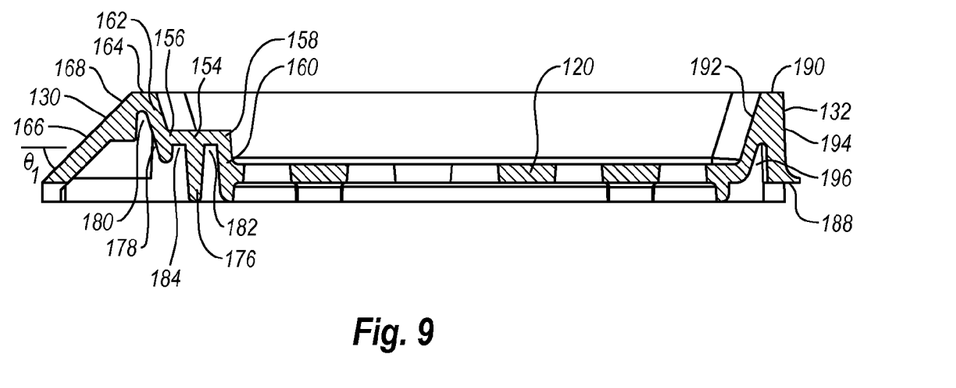
FIG. 9 is a longitudinal cross sectional side view of the base of the tissue cassette shown in FIG. 2.

Turning to FIG. 9, front wall 130 comprises a horizontally extending platform 154 that extends between a first end 156 and an opposing second end 158. A lower wall portion 160 outwardly slopes from floor 120 to second end 158 of platform 154. An upper wall portion 162 outwardly slops from first end 156 of platform 154 to a top end face 164. A marking wall 166 extends between side walls 134 and 136 and projects down and away from top end face 164. Marking wall 166 has a substantially planer outside face 168 that is typically disposed at an angle $\theta_1$ relative to the horizontal in a range between about 30° to about 60° with about 40° to about 50° being more common. Other angles can also be used. Outside face 168 is configured so that a label, printing, marking, barcode or other forms of indicia can be placed thereon for identifying the tissue specimen.

Figure 10:
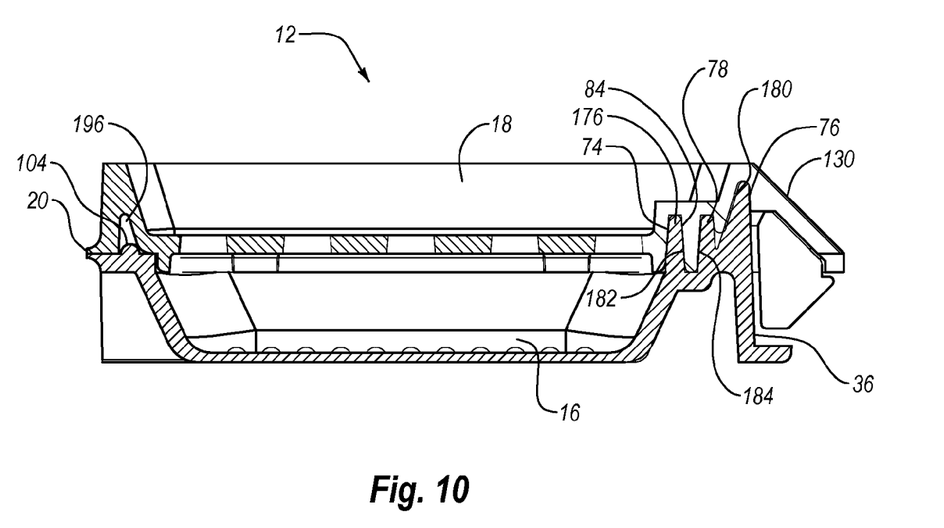
FIG. 10 is a longitudinal cross sectional side view of tissue cassette shown in FIG. 4.

A sealing ridge 176 downwardly projects at a central location from platform 154 while a sealing ridge 178 downwardly projects from platform 154 at first end 156. A sealing slot 180 is formed between upper wall portion 162 and marking wall 166 while sealing slots 182 and 184 are formed on opposing sides of sealing ridge 176. Sealing slots 182 and 184 inwardly taper and are configured substantially complimentary to sealing ridges 74 and 78 (FIG. 6). Sealing ridge 176 inwardly tapers as it downwardly projects and is configured substantially complimentary to sealing slot 84 on mold 16 (FIG. 6). However, sealing ridges 74, 76, 78, 176, and 178 are dimensioned slightly larger than sealing slots 180, 182, 184, 84 and 86 so that the sealing ridges create an interference fit within the sealing slots as tissue cassette 12 is moved to the closed position as shown in FIG. 10. The interference fit between the sealing slot and sealing ridges on front walls 36 and 130 for a seal that prevents molten wax from leaking out therebetween. It is appreciated that the multiple sealing slots and sealing ridges on front walls 36 and 130 can be replaced with a single sealing ridge and sealing slot to affect a seal. However, because front walls 36 and 130 is where mold 16 and base 18 latch together, having multiple interlocking sealing ridges and sealing slots improves sealing between front walls 36 and 130.

Returning to FIG. 9, back wall 132 longitudinally extends between opposing side walls 134 and 136 and includes a bottom end face 188 and an opposing top end face 190 with an inside face 192 and an opposing outside face 194 each extending therebetween. A sealing slot 196 is recessed on bottom end face 188 and inwardly tapers as it extends from bottom end face 188 toward top end face 190. Sealing slot 196 is configured to receive and form an interference fit with sealing ridge 104 of mold 16 as tissue cassette 12 is moved to the closed position as shown in FIG. 10. This interference fit in conjunction with hinge 20 prevent leakage of molten wax therebetween.

Figure 11:
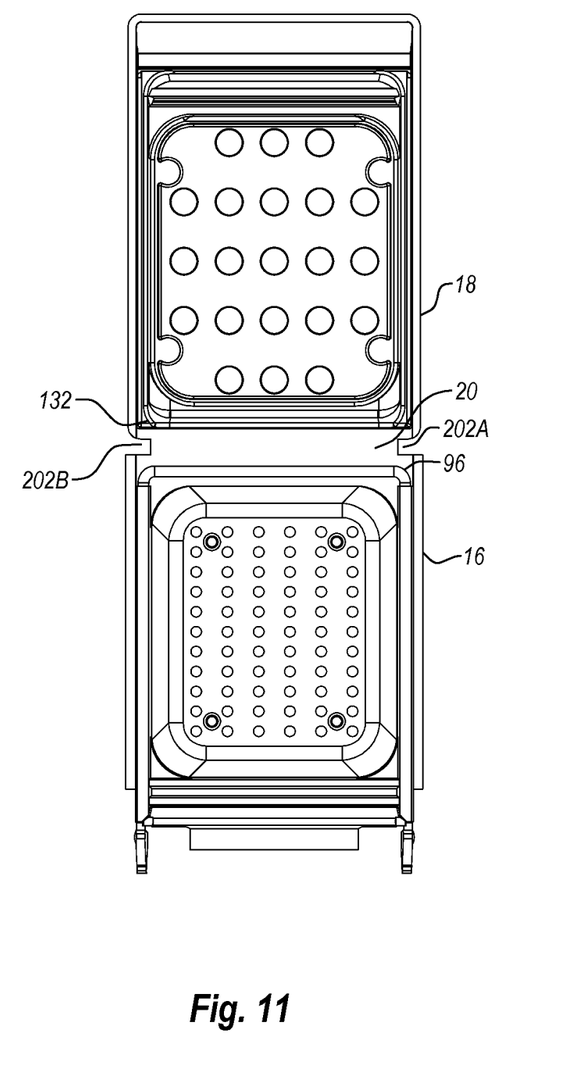
FIG. 11 is a top plan view the tissue cassette shown in FIG. 2.

As shown in FIGS. 2 and 11, hinge 20 extends between back wall 96 of mold 16 and back wall 132 of base 18. Hinge 20 longitudinally extends along the length of back walls 96 and 132 and has a notch 202A and 202B formed at opposing ends thereof. In the embodiment depicted, hinge 20 is a living hinge that is integrally formed as a single unitary structure with mold 16 and base 18. Typically, hinge 20 is designed so that it will fail after tissue cassette 12 is moved between the open and closed position between six to ten times and can otherwise be easily torn or broken along its length. This is because, as will be discussed below in greater detail, it is desirable that after the tissue sample is embedded in wax to separate mold 16 from base 18 so that base 18 can be mounted to the microtome for tissue sectioning. Living hinge 20 typically has a thickness in a range between about 0.05 inches to about 0.02 inches. Other dimensions can also be used. In alternative embodiments, hinge 20 can be separately connected to mold 16 and/or base 18 such as through adhesive, welding, fasteners, or the like, and alternatively can comprise other types of hinges such as a pinned hinge.

It is desirable that tissue cassette 12 is securely held in the closed position so that it does not inadvertently open during processing. Such opening could result in causing the tissue sample to be dropped, damaged, or lost. The interference fit between the sealing ridges and sealing slots as discussed above assists in securing mold 16 and base 18 together when in the closed position. In one embodiment of the present invention, however, means are provided for releasably latching base 18 to mold 16 when tissue cassette 12 is in the closed position. By way of example and not by limitation, as depicted in FIG. 2, a pair of locking arms 210A and 210B outwardly project from front wall 36 of mold 16 at opposing ends thereof. Each locking arms 210 comprises a flex arm 212 projecting from front wall 36 and a head 214 mounted on the end thereof. Head 214 is shown as having a substantially triangular configuration with an outside face 216. Outwardly projecting from outside face 216 is a detent 218.

A receiver 220A and 220B is formed on face 150 and 150' of sidewalls 134 and 136, respectively. Receivers 220 are designed to receive detents 218 when tissue cassette 12 is in the closed position so that tissue cassette 12 is releasably held in the closed position. That is, as tissue cassette 12 is moved into the closed position, locking arms 210A and B resiliently flex inward as sidewalls 134 and 136 pass over them. When detents 218 align with receivers 220, locking arms 210 resiliently flex outward forcing detents 218 into receivers 220. In the depicted embodiment, receivers 220 comprise apertures that extend all the way through sidewalls 134 and 136. In an alternative embodiment, receivers 220 can comprise recesses formed faces 150 and 150'. One of the benefits of the disclosed latching system is that outside face 168 of marking wall 166 (FIG. 3) remains in an unobstructed plane. That is, there are no members projecting up from face 168 or the ends thereof. As such, marking wall 166 can be placed in a printer or other marking apparatus for applying printing thereon without being obstructed. In other embodiments, it is appreciated that other clamps, catches, and other fasteners known in the art for latching together hinged structures can be used.

Tissue cassette 12 is made from materials that will withstand the processing fluids, such as fixatives, alcohols, xylenes, other aromatic hydrocarbon and aliphatic hydrocarbons and petroleum distillates, and the embedding material, such as molten paraffin. Examples of materials that can be used to form tissue cassette 12 include the polyoxymethylene family of thermoplastics including acetal homopolymers, acetal copolymers, polyacetal, and polyformaldehyde. Once specific example of an acetal copolymer that can be used is CELCON M270 available from Ticona. Because of the corrosive nature of the processing fluids, it is appreciated that conventional gaskets and seals cannot be used to form the seal between mold 16 and base 18. As such, the sealing discussed above through the use of sealing ridges and sealing slots is unique in part because the sealing ridges and sealing slots can be made from materials that withstand the processing fluids and can also be made from the same material as the remainder of tissue cassette 12. This enables the entire tissue cassette 12 to be easily molded as a single unitary structure, thereby reducing processing costs. In the closed position, as shown in FIG. 4, tissue cassette 12 typically has a height H in a range between about 0.35 inches to about 0.75 inches, a length L in a range between about 1.4 inches to about 2 inches, and a width W in a range between about 1 inch to about 1.5 inches. As depicted in FIG. 8, tissue compartment 206 is bounded between floors 22 and 120 and typically has a volume in a range between about 0.0280 to about 0.0350 $in^3$. Other volumes can also be used.

FIGS. 13-17 show different views of cassette 12 in the open position. FIG. 18-24 show different views of cassette 12 in the closed position.

Returning to FIG. 1, sponge 14 is secured to inside face 122 of floor 120 of base 18. Sponge 14 is typically attached by a cyanacrylate-based adhesive, such as the LOCK-TITE family of cyanacrylate adhesives, most commonly, LOCK-TITE 401. However, other fastening techniques such as welding, fasteners or the like can also be used. Spacers 224 can be formed extending from floor 120 adjacent the perimeter edge to assist in centering sponge 14 on floor 120. Sponge 14 is typically made from a closed cell, non-reticulated sponge having a destiny range that ensures that tissue samples "stand proud" of sponge 14, yet compress when necessary. This helps to ensure that tissue samples of different sizes can be placed on the same plane on floor 22 of mold 16. Sponge 14 is made from a material that will not dissolve or otherwise deteriorate in standard processing chemicals such as alcohols, xylenes, and molten paraffin. To this end, sponge is typically made from a polyester or polyurethane.

It is also desirable that sponge 14 maintain its physical dimensions yet allow for some flexibility to maintain tissue integrity. To achieve this objective, sponge 14 typically has a density of 2 $lb/ft^3$ with a tolerance of +/−10%, a porosity of 75 ppi (pores per inch) with a tolerance of +/−20%, a tensile strength of 25 $lb/in^2$ with a tolerance of +/−10%, an elongation before failure of 260% with a tolerance of +/−10%, a tear strength of 2.70 lb/in with a tolerance of +/−20%, a compression load deflection at 25% deflection of 0.50 $lb/in^2$ with a tolerance of +/−10%, a compression load deflection at 50% deflection of 0.60 $lb/in^2$ with a tolerance of +/−10%, and a compression set at 50% deflection of 35% with a tolerance of +/−10%. It is further desirable that sponge 14 allow adequate flow of air and fluids such that tissues are properly processed. To help achieve this sponge 14 typically has an air flow of 20 $ft^3/ft^2/min$ with a tolerance of +/−10%.

It is desirable that sponge 14 not stain with standard stains used in histology or cause artifacts on the sample slides. As such, sponge 14 is typically non-reticulated. Reticulated sponges are altered during the reticulation process and can often stain with standard stains. Furthermore, because the reticulation process removes or breaks down portions of the walls of the closed cells of the foam, reticulated sponges are significantly more likely to leave sponge artifacts on the tissue specimen. Such artifacts can hinder analysis of the tissue sample.

During use of sponge 14 it is desirable that the tissue specimens be easily visualized on sponge 14. To help optimize this visualization, the color choices for sponge 14 are typically limited to pastel green, blue, or purple, although other colors can also be used.

Finally, the length and width dimension of sponge 14 depend on the size of tissue cassette 12. However, the length and width dimensions are typically maximized for the most possible area for specimen grossing and orientation, but not so large as to hinder fluid dynamics, cover micro holes 32 (FIG. 3), or prevent proper locking of the latching mechanism as discussed above. The thickness should also be large enough to maintain tissue orientation, but not so thick as to impact tissue sectioning at the microtome. In one embodiment, sponge 14 has a width in a range between about 0.60 to about 0.80 inches, a length in a range between about 0.80 to about 1.0 inches and a height in a range between about 0.017 to about 0.019 inches.

Figure 12:
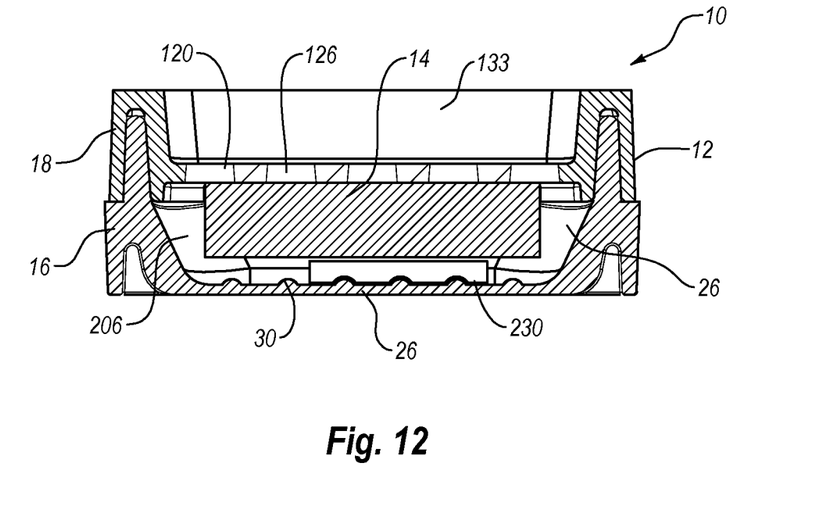
FIG. 12 is a lateral cross sectional side view of the tissue cassette assembly shown in FIG. 1 in the closed position with a tissue sample.
Figure 13:
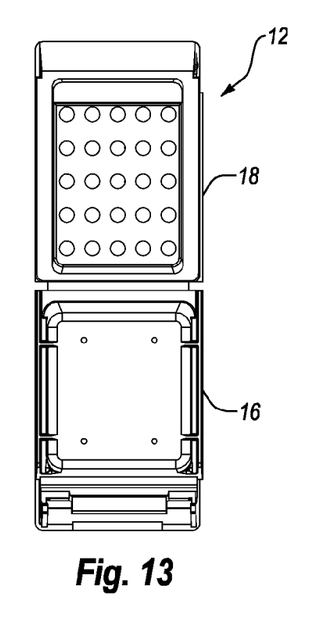
FIG. 13 is a bottom plan view of the tissue cassette shown in FIG. 2.
Figure 14:
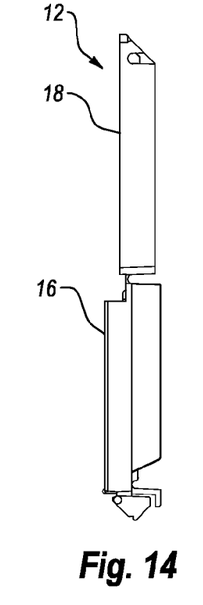
FIG. 14 is an elevated left side view of the tissue cassette shown in FIG. 11.
Figure 15:
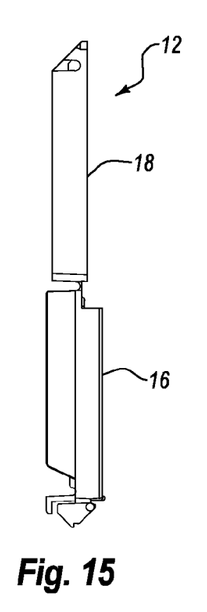
FIG. 15 is an elevated right side view thereof.
Figure 16:
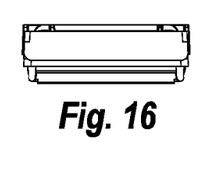
FIG. 16 is an elevated front view thereof.
Figure 17:
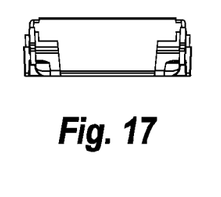
FIG. 17 is an elevated back view thereof.
Figure 18:
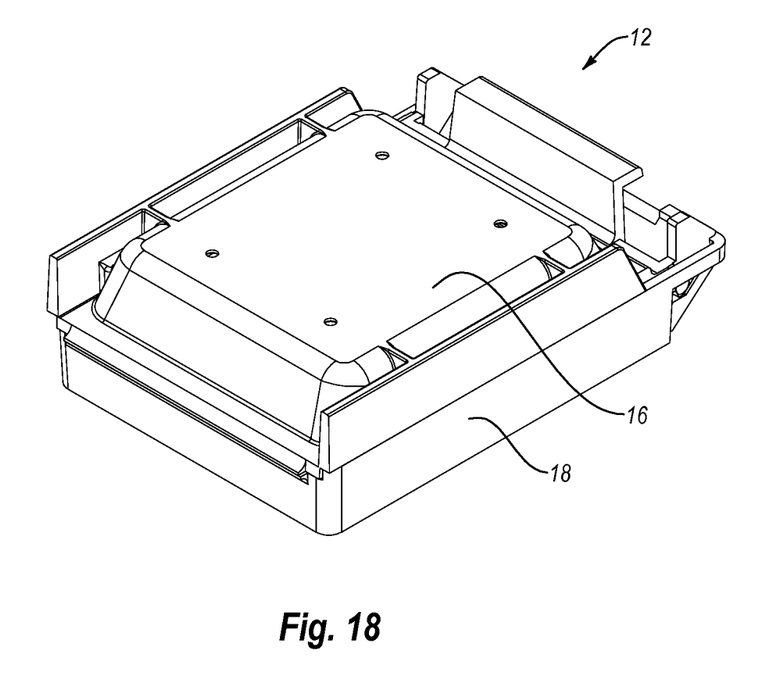
FIG. 18 is a bottom perspective view of the tissue cassette shown in FIG. 4 in the closed position.
Figure 19:
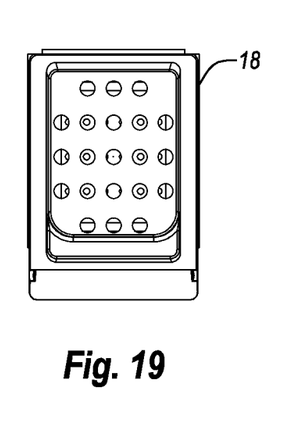
FIG. 19 is a top plan view of the tissue cassette shown in FIG. 18.
Figure 20:
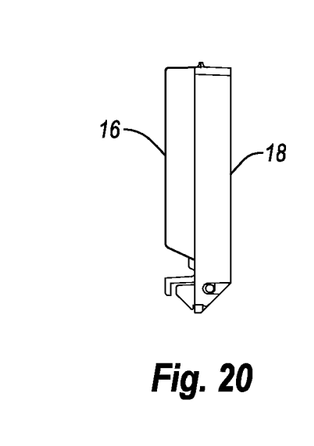
FIG. 20 is an elevated right side view thereof.
Figure 21:
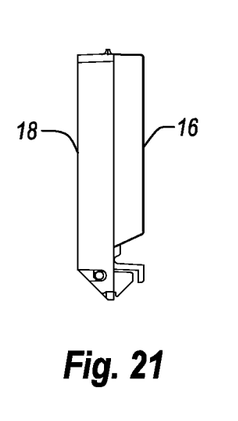
FIG. 21 is an elevated left side view thereof.
Figure 22:
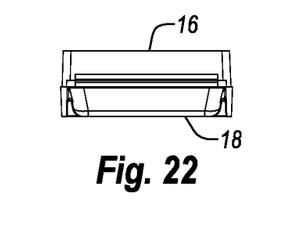
FIG. 22 is an elevated front end view thereof.
Figure 23:
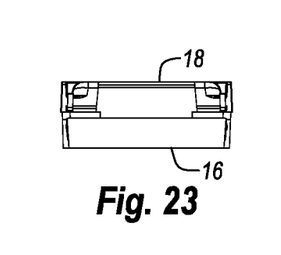
FIG. 23 is an elevated back view thereof.
Figure 24:
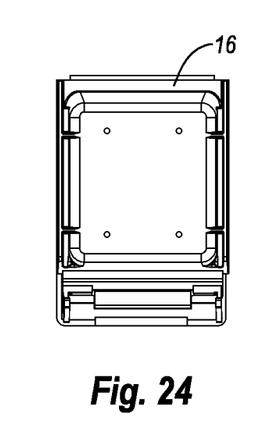
FIG. 24 is a bottom plan view thereof.

During use, a tissue sample 230 is placed on floor 26 of mold 16 and tissue cassette 12 is moved into the closed position as shown in FIG. 12. As tissue cassette 12 is closed, sponge 14 pushes the tissue sample against floor 26 so that the tissue sample is securely held in position and properly orientated. Depending on the size of the tissue sample, sponge 14 may compress some amount. Either before or after the tissue sample 230 is secured within tissue cassette 12, indicia is placed on marking wall 166 (FIG. 3) that identifies the tissue sample. This is typically accomplished by using tissue cassette 12 with a specially adapted printer or label machine but can also be accomplished by manually printing the indicia or applying a label to making wall 166. Other conventional techniques can also be used.

Various solvents are now applied to the marked tissue cassette 12 containing tissue sample 230 so as to remove the water content from tissue specimen 230. In one embodiment this is accomplished by placing tissue cassette 12 within a processing chamber. The solvent fluids, such as various alcohols and xylenes, are then sequentially pumped into the processing chamber. The solvents enter the closed cassette 12 through openings 126 on base 18 and through micropores 32 on mold 16 so as to fill tissue compartment 206. The solvents flow through sponge 14 so that all of tissue sample 230 resting against sponge 14 is exposed to the solvents. Likewise, projections 30 on floor 22 of mold 16 enable the solvents flow underneath tissue sample 230 so that tissue sample 230 can be completely encircled by the solvents.

After tissue sample 230 is exposed to one solvent, the solvent is removed from the processing chamber and the next solvent is pumped into the processing chamber. This process is repeated until tissue sample 230 is exposed to the desired number of solvents to remove the water content from tissue sample 230. Because of the properties of sponge 14, there is reduced carryover of solvents relative to more conventional sponges. That is, as a result of the combination of appropriately controlled pore size (porosity), material density, elasticity, air flow and compression load set, less processing reagents are retained within the sponge to contaminate the next reagent. Part of the reduction in carry over is the reduction in sponge volume that is being utilized, as there can be a 58% reduction in sponge material utilized. However, the unique and tightly controlled properties of the new sponge, as stated above, allow the sponge to only expand in one example by 16% of its original volume when exposed to processing reagents. This is a reduction in fluid retention of 45%. The combination of reduction in sponge volume and in fluid retention combine together in one example to reduce total reagent carryover by 68%.

In addition, there is less solvent retained within sponge 14 so that there is less of one solvent carried over into the next solvent. Each solvent is typically collected after use and stored for reuse. However, the carryover of one solvent into the next solvent contaminates or dilutes the later solvent. This contamination eventually requires the later solvents to be replaced with a clean solvent to achieve the required processing of tissue sample 230. Accordingly, by having less carryover of solvents, there is less contamination of the latter solvents and thus the latter solvents can be used for a longer period. This results in a cost savings in that the solvents are expensive to purchase and dispose of.

Continuing with FIG. 12, once the water content is removed from tissue sample 230, tissue cassette 12 is removed from the processing chamber. A molten wax, such as molten paraffin, is then poured into base cavity 133. The molten wax passes down through large opening 126 on floor 120 of base 18 so as to again fill tissue compartment 206 and surround tissue sample 230. As previously mentioned, as a result of the engagement between the various sealing slots and sealing ridges on mold 16 and base 18, a seal is formed between mold 16 and base 18 that is sufficient to prevent the molten wax from leaking out between mold 16 and base 18. Likewise, micropores 32 (FIG. 3) on mold 16 are intentionally designed to be very small so that only a minimal amount of molten wax can pass therethrough.

Either prior to or after the molten wax is poured into tissue compartment 206, tissue cassette 12 is placed on a cold surface, such as a cooling plate, that is sufficient to solidify molten wax. In turn, the cold surface solidifies the molten wax within micropores 32 so as to prevent the wax from further leaking out through micropores 32. Once micropores 32 are closed, the reminder of the molten wax is allowed to cool and solidify so that tissue sample 230 is embedded within the wax. In some prior art embodiments of tissue cassettes, the molten wax can freely flow through the floor of the cassette and through the aligned sidewalls. As such, the cassettes must be placed in a tray that holds the molten wax and enables the wax to fill the tissue cassette. The inventive design incorporating micropores 32 and the sealing engagement between mold 16 and base 18 eliminates the need to use a separate tray because minimal if any wax is leaked out tissue cassette 12. That is, the molten wax can be poured into tissue cassette 12 without the use of a separate tray and with only minimal loss of wax through micropores 32. As such, the inventive system eliminates the need for separate trays, eliminates the mess and waste associated with molten wax flowing into the separate trays, and eliminates the wasted time associated with using the separate trays.

Once the wax has solidified within tissue cassette 12, tissue cassette 12 is moved to the open position. In so doing, the solidified wax encasing tissue sample 230 is pulled out of mold cavity 26 and is retained on base 18. This retention is accomplished by filling the molten wax to a level above floor 120 within base cavity 133 so that the wax when solidified forms a strong supporting matrix that extends through and is secured to floor 120. Mold 16 can then be broken away from base 18 by breaking or tearing hinge 20. Finally, base 18 can be directly secured to a microtome, such as by securing to a chuck thereof. The microtome can then be used to cut sections of tissue sample 230 embedded within the wax projecting from base 18.

It is appreciated that because marking wall 166 is part of base 18, the label, barcode or other indicia attached thereto that identifies tissue sample 230 always stays with tissue sample 230 from the time it is inserted within tissue cassette 12 through the time of sectioning on the microtome. That is, the sample identifier is constantly maintained with tissue sample 230 through the steps of grossing, processing, embedding, and microtomy. Furthermore, tissue cassette 12 is never opened once tissue sample 230 is closed therein until after tissue sample 230 is embedded. As a result, the inventive system minimizes any chance that tissue sample 12 can be lost or separated from its identifier.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tissue cassette comprising:
   a mold comprising a first floor encircled by a first perimeter wall extending upward from the first floor, the first floor and first perimeter wall bounding a mold cavity, the first floor having at least one micropore extending therethrough, the at least one micropore having a maximum diameter less than 0.040 inches;
   a base comprising a second floor encircled by a second perimeter wall extending upward from the second floor, the second floor and second perimeter wall bounding a base cavity, the second floor having a plurality of spaced apart openings extending therethrough; and
   a living hinge coupling the base to the mold to allow the tissue cassette to be moved between an open position and a closed position, the living hinge enabling the base and the mold to be moved between the open and closed position, wherein when the tissue cassette is in the closed position the base cavity is positioned directly above the mold cavity with the second floor being disposed between the base cavity and the mold cavity, and wherein the base, mold, and living hinge are integrally formed as a single unitary structure.

2. The tissue cassette as recited in claim 1, wherein the at least one micropore comprises a plurality of spaced apart micropores in a range from two micropores to eight micropores each extending through the first floor and each having a maximum diameter less than about 0.040 inches.

3. The tissue cassette as recited in claim 2, wherein the only passages extending through the first floor are the micropores.

4. The tissue cassette as recited in claim 1, wherein each of the spaced apart openings extending through the second floor have a maximum diameter that is greater than 0.110 inches.

5. The tissue cassette as recited in claim 1, further comprising a sponge secured to the second floor of the base so that the sponge is disposed within the mold cavity when the base and mold are in the closed position.

6. The tissue cassette as recited in claim 1, further comprising a releasable latch that secures the base to the mold when in the closed position.

7. The tissue cassette as recited in claim 1, wherein the first floor comprises an inside face adjacent the mold cavity and an opposing outside face opposite the mold cavity, the at least one micropore extending between the inside face and the opposing outside face, the inside face having a sub-surface that is substantially planar and a plurality of spaced apart projections upstanding directly from the sub-surface.

8. The tissue cassette as recited in claim 1, wherein the second perimeter wall has a bottom end face and an opposing top end face, the bottom end face bounding a sealing slot that extends longitudinally along a length of the second perimeter wall and that progressively inwardly tapers as it extends from the bottom end face toward to the upper end face, the first perimeter wall comprising a tapered sealing ridge extending along a length thereof such that in the closed position the sealing ridge is received in an interference fit within the sealing slot so that a seal is formed therebetween.

9. A tissue cassette comprising:
   a mold that comprises a first floor encircled by a first perimeter wall extending upward from the first floor, the first floor and first perimeter wall bounding a mold cavity, the first floor having an inside face and an opposing outside face, the inside face having a sub-surface that is substantially planar and a plurality of spaced apart projections upstanding from the sub-surface, the first floor having a plurality of spaced apart micropores in a range from two micropores to eight micropores each extending therethrough, each of the micropores having a maximum diameter in a range between 0.030 to 0.040 inches, wherein the only passages extending through the first floor are the micropores;
   a base that comprises a second floor encircled by a second perimeter wall extending upward from the second floor, the second floor and second perimeter wall bounding a base cavity, the second floor having an inside face and an opposing outside face and having a plurality of spaced apart openings extending therethrough; and
   a living hinge coupling the base to the mold to allow the tissue cassette to be selectively folded between an open position and a closed position, wherein, in the closed position, the base cavity overlies the mold cavity with the second floor being disposed between the base cavity and the mold cavity and a tissue compartment is formed between the inside face of the first floor and the outside face of the second floor, wherein the base, mold, and living hinge are integrally formed as a single unitary structure.

10. The tissue cassette as recited in claim 9, wherein the second perimeter wall has a bottom end face and an opposing top end face, the bottom end face bounding a sealing slot that extends longitudinally along a length of the second perimeter wall and that progressively inwardly tapers as it extends from the bottom end face toward to the upper end face, the second perimeter wall comprising a back wall, an opposing front wall, and opposing sidewalls extending therebetween, the sealing slot extending along the front wall and the opposing sidewalls,
   the first perimeter wall having a tapered sealing ridge extending along a length thereof such that in the closed position the sealing ridge is received in an interference fit within the sealing slot so that a seal is formed therebetween, the first perimeter wall comprising a back wall, an opposing front wall, and opposing sidewalls extending therebetween, the tapered sealing ridge extending along the front wall and the opposing sidewalls.

11. The tissue cassette as recited in claim 9, further comprising a latching system releasably securing the base to the mold when the base and the mold are in the closed position, the latching system comprising:
   a flexible arm projecting from a front wall of the mold, the flexible arm having an outside face with a detent formed thereon; and
   a receiver recessed on or extending through a portion of one of sidewalls of the base, the detent being received within the receiver when the base and the mold are in the closed position.

* * * * *